(12) United States Patent
Barkoczy et al.

(10) Patent No.: US 7,186,848 B2
(45) Date of Patent: Mar. 6, 2007

(54) POLYMORPHS OF A 1-PYRROLE DERIVATIVE, INTERMEDIATE FOR THE PREPARATION OF ATORVASTATIN

(75) Inventors: Jozsef Barkoczy, Budapest (HU); Gyula Simig, Budapest (HU); Zoltan Greff, Budapest (HU); Peter Kotay Nagy, Vac (HU); Zsuzsa Szent Kirallyi, Budapest (HU); Ferenc Bartha, Tiszavasvari (HU); Györgyi Vereczkeyne Donath, Budapest (HU); Kalman Nagy, Budapest (HU)

(73) Assignee: EGIS Gyogyszergyar Rt., Budapest (HU)

( * ) Notice: Subject to any disclaimer, the term of this patent is extended or adjusted under 35 U.S.C. 154(b) by 24 days.

(21) Appl. No.: 10/489,686

(22) PCT Filed: Sep. 13, 2002

(86) PCT No.: PCT/HU02/00088

§ 371 (c)(1),
(2), (4) Date: Jun. 2, 2004

(87) PCT Pub. No.: WO03/024959

PCT Pub. Date: Mar. 27, 2003

(65) Prior Publication Data

US 2004/0249168 A1    Dec. 9, 2004

(30) Foreign Application Priority Data

Sep. 14, 2001  (HU) .................................. 0103702

(51) Int. Cl.
C07D 405/06       (2006.01)
(52) U.S. Cl. ..................................... 548/517
(58) Field of Classification Search ................ 548/517
See application file for complete search history.

(56) References Cited

U.S. PATENT DOCUMENTS 5,003,080 A  *  3/1991  Butler et al. ................ 548/517
5,103,024 A  *  4/1992  Millar et al. ................ 549/373

FOREIGN PATENT DOCUMENTS

WO    WO 02/059087 A1  *  8/2002

OTHER PUBLICATIONS

US Pharmacopia #23, National Formulary #18 (1995).*
Brittain, Polymorhphism in Pharmaceutical Solids, Marcell Dekker, p. 235-236 (1995).*

* cited by examiner

Primary Examiner—Joseph K. McKane
Assistant Examiner—Andrew B. Freistein
(74) Attorney, Agent, or Firm—Andrew Wilford; Jonathan Myers

(57) ABSTRACT

The invention relates to new crystalline forms I and II of (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester of the Formula (I) and a process for the preparation thereof. The new polymorphs of the present invention are useful pharmaceutical intermediates which can be used in the preparation of the hydroxymethyl-glutaryl coenzyme (HMG-COA) reducing enzyme inhibitor having the INN (International Non-proprietory Name) atorvastatin (I)

7 Claims, 2 Drawing Sheets

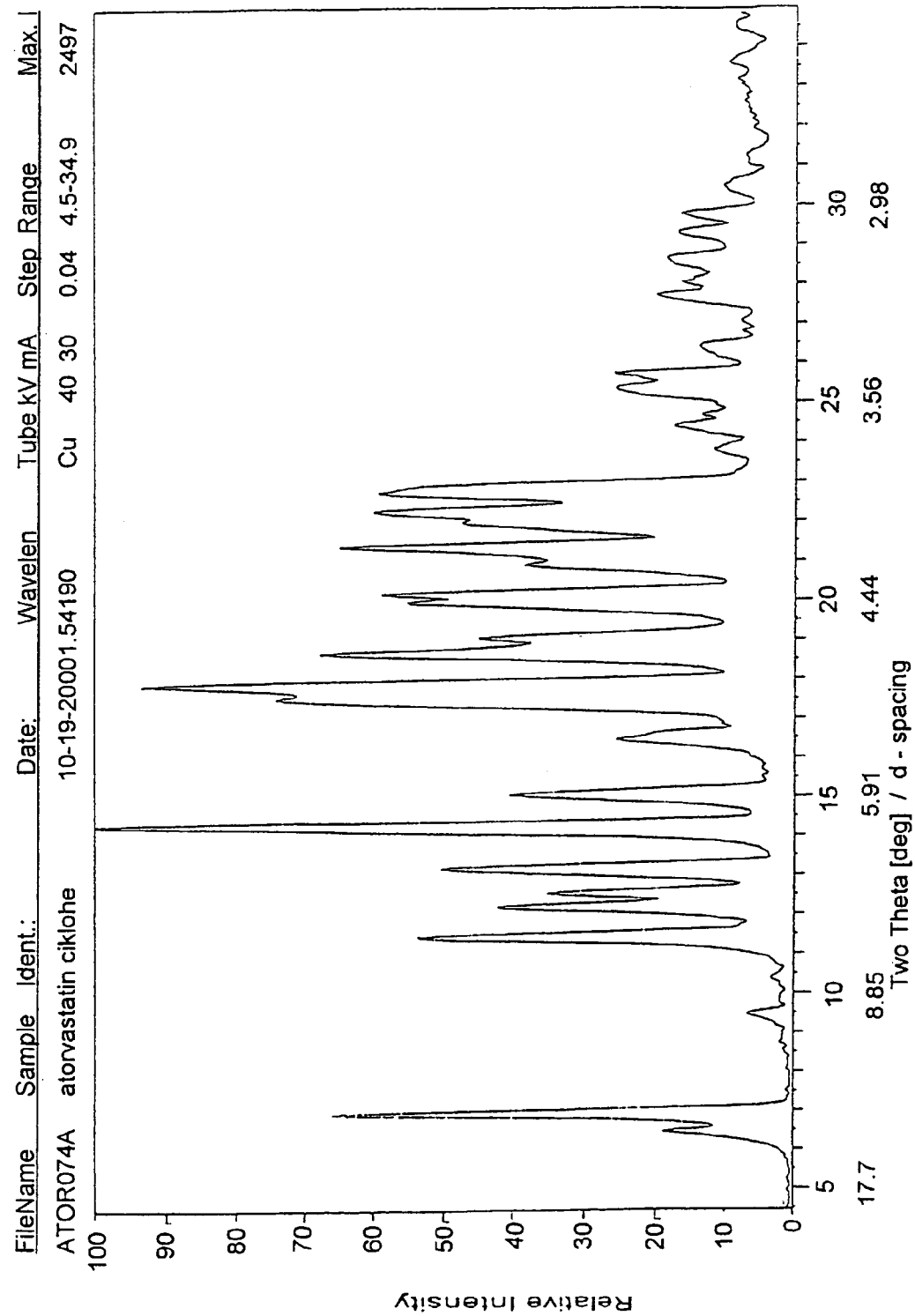

Figure 1:
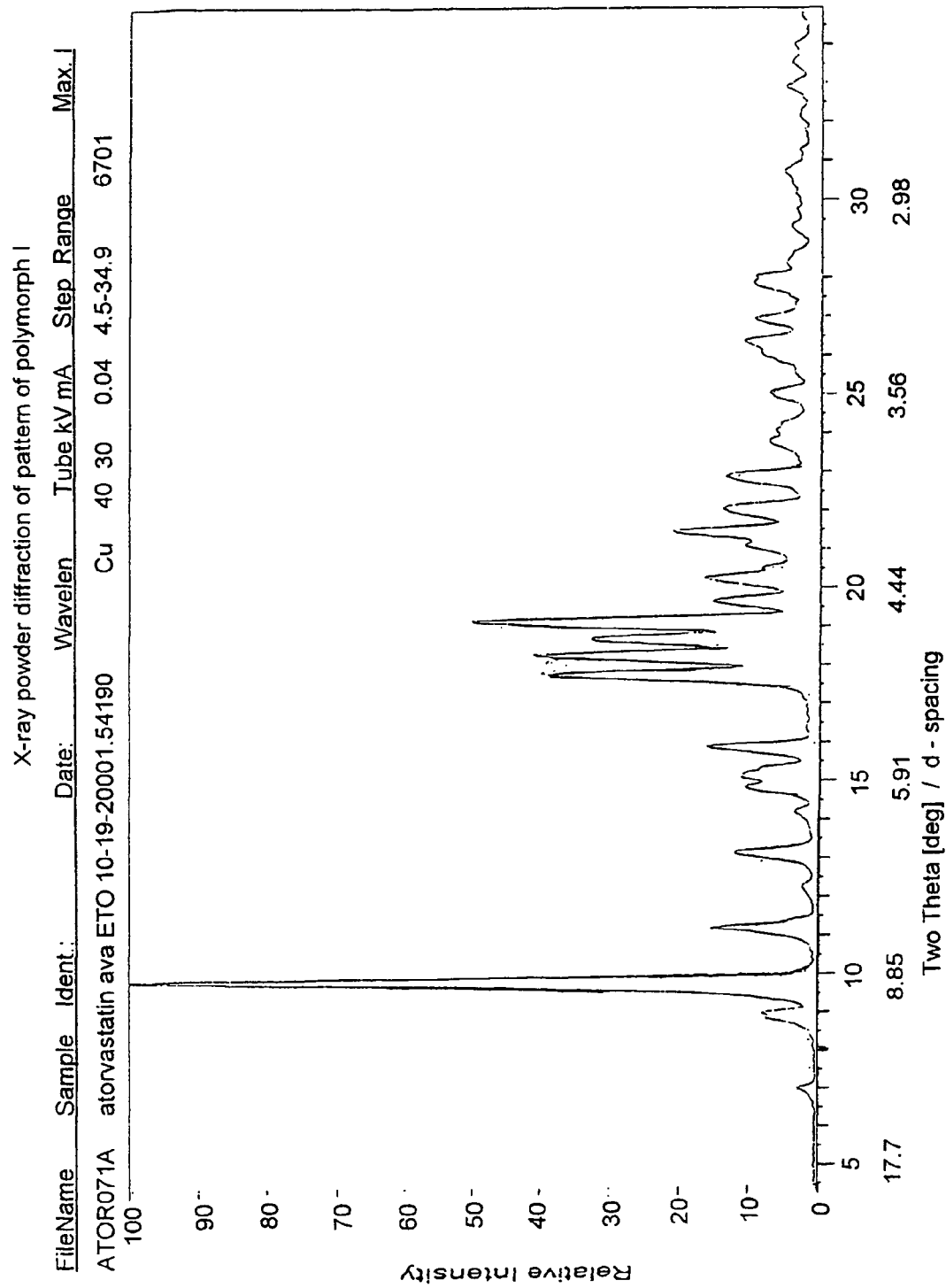

POLYMORPHS OF A 1-PYRROLE DERIVATIVE, INTERMEDIATE FOR THE PREPARATION OF ATORVASTATIN

This is a National filing under 35 U.S.C. § 371 of PCT/HU02/00088, filed Sep. 9, 2002.

FIELD OF THE INVENTION

This invention relates to new polymorphs of (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and a process for the preparation thereof.

More particularly the invention is concerned with new crystalline forms I and II of (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and a process for the preparation thereof.

TECHNICAL BACKGROUND (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester of the Formula

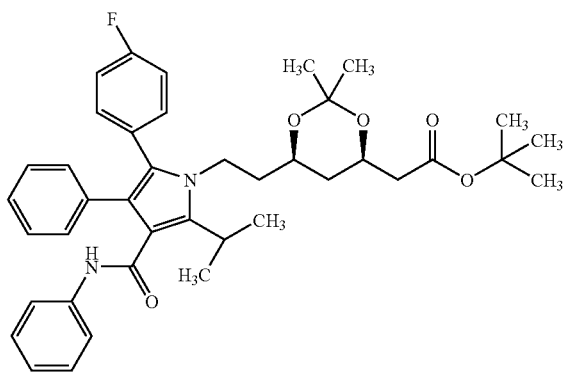

is a known and valuable pharmaceutical intermediate useful in the preparation of the HMG-CoA [hydroxymethyl-glutary-coenzyme reducing enzyme inhibitor (3R,5R)-3,5-dihydroxy-[3-phenyl-4-(phenylamino)-carbonyl]-2-(4-fluoro-phenyl)-5-(1-methyl-ethyl)-1H-pyrrol-1-yl-ethyl-heptanoic acid-hemicalcium salt] having the INN (International Non-Proprietary Name) atorvastatin.

TECHNICAL BACKGROUND (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester of the Formula I was described in EP-B 330,172. According to said patent (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester of the Formula I is prepared by reacting (4R-cis)-1,1-dimethyl-ethyl-6-(2-amino-ethyl)-2,2-dimethyl-1,3-dioxane-4-acetate of the Formula

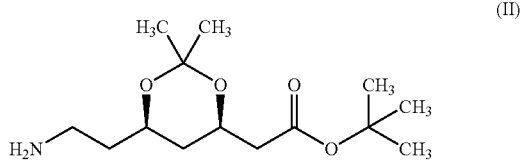

with 2-[1-phenyl-2-(4-fluoro-phenyl)-2-oxo-ethyl]-4-methyl-N-methyl-N-phenyl-3-oxo-pentanamide of the Formula

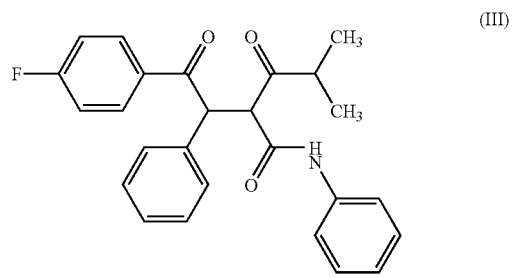

in a 9:1 mixture of heptane and toluene under heating to boiling for 24 hours, cooling the reaction mixture, adding some 2-propanol and isolating the precipitated product by filtration. The reference is silent in disclosing the melting point of the product and the crystal form of the product is not mentioned either.

According to U.S. Pat. No. 5,103,024 the reaction is carried out as described in EP-B 330,172 except that a 9:1 mixture of toluene and heptane is used; the reaction mixture is then heated to boiling for 24 hours, cooled, some 2-propanol is added and the precipitated compound of the Formula I is isolated by filtration. Nothing is disclosed about the melting point and crystal form is the product.

In U.S. Pat. No. 5,155,251 the working example of EP-B 330,172 is disclosed. This reference contains no teaching on the melting point and crystal form of the compound of the Formula I.

According to Tetrahedron Letters Vol. 33. Np. 17, 2283-2284 (1992) the reaction of the compounds of the Formulae II and III is carried out in a 1:4:1 mixture of toluene, heptane and tetrahydrofurane in the presence of pivalic acid as catalyst. The isolation of the product from the reaction mixture is not described, nor is it disclosed whether the compound of the Formula I is formed in solid form.

Recently a strong demand has arisen for pure and morphologically uniform products. Technological procedures more and more require products which possess constant, stable and identical filtration and drying properties. Because of economical reasons there is a need for morphologically uniform products which can be prepared by methods readily feasible on industrial scale, suitable for scaling-up and providing a product of constantly identical crystalline form.

It is known that amorphous products can be difficultly filtered and dried, the scaling-up of the manufacturing process is encountered with considerable difficulties and the stability of the product is not satisfactory either.

SUMMARY OF THE INVENTION

The object of the invention is the development of new crystalline forms of (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester which are easy to be filtered and dried, are stable for a long period of time and can be satisfactorily stored.

The above object is solved by the present invention.

The invention is based on the recognition that (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester of the Formula I can be prepared in two morphologically uniform polymorph crystalline forms which meet the above requirements.

Said new morphologically uniform polymorphs are designated as polymorphs I and II in the patent specification and the claims.

DETAILS OF THE INVENTION

According to an aspect of the present invention there is provided crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester characterized by the X-ray powder diffraction pattern expressed in Table 1 and FIG. 1, measured using $CuK_\alpha$ radiation:

TABLE 1

Position of diffraction lines and relative intensities (>10% of polymorph I)

| Peak No. | 2*th [deg] | d(hkl) [Å] | I(abs) [cts] | I(rel) [%] |
|---|---|---|---|---|
| 1 | 9.85 | 8.9800 | 6701 | 100.00 |
| 2 | 11.20 | 7.8983 | 996 | 14.86 |
| 3 | 13.14 | 6.7401 | 771 | 11.51 |
| 4 | 15.89 | 5.5793 | 1043 | 15.56 |
| 5 | 17.76 | 4.9940 | 2565 | 38.28 |
| 6 | 18.29 | 4.8508 | 2710 | 40.44 |
| 7 | 18.69 | 4.7483 | 2152 | 32.11 |
| 8 | 19.17 | 4.6300 | 3325 | 49.62 |
| 9 | 19.66 | 4.5155 | 983 | 14.67 |
| 10 | 20.24 | 4.3865 | 10064 | 15.88 |
| 11 | 21.10 | 4.2107 | 671 | 10.01 |
| 12 | 21.49 | 4.1351 | 1362 | 20.33 |
| 13 | 22.05 | 4.0310 | 889 | 13.27 |
| 14 | 22.90 | 3.8836 | 863 | 12.88 |
| 15 | 26.41 | 3.3749 | 681 | 10.16 |
| 16 | 26.95 | 3.3080 | 597 | 8.91 |
| 17 | 27.89 | 3.1995 | 612 | 9.13 |

The powder diffraction pattern of new crystalline polymorph I is determined under the following conditions:

Equipment: PHILIPS-XPERT PW 3710 powder diffractometer
Radiation: CuKα (λ: 1.54190Å)
Monochromator: graphite
Exciting voltage: 40 kV
Anode current: 30 Ma
Standard reference substance: SRM 675
Mica Powder (synthetic fluorographite), Ser. No.: 981307.
The measurement is continuous: Θ/2Θ scan: 4.5°-35.00° 2Θ
Step size: 0.04°
Sample: surface plain, width 0.5 mm, in quartz sample holder, measured and stored at room temperature.

According to a further aspect of the invention there is provided a process for the preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester which comprises a) dissolving amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester in an inert solvent under heating, and thereafter crystallizing and isolating the crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester; or b) dissolving crystalline form II (4R-cis)-6-[2-[3-phenyl-4-(phenyl-carbamoyl)-2-(4-fluoro-phenyl)-5-(1-methyl-ethyl) -pyrrol-1-yl]-ethyl]-2,2-dimethyl-[1,3]dioxane-4-yl-acetic acid-tertiary butyl ester in an inert solvent under heating, and thereafter crystallizing and isolating the crystalline form I (4R-cis)-6-[2-[3-phenyl-4-(phenyl-carbamoyl)-2-(4-fluoro-phenyl)-5-(1-methyl -ethyl)-pyrrol-1-yl]-ethyl]-2,2-dimethyl -[1,3]dioxane-4-yl-acetic acid-tertiary butyl ester; or c) suspending amorphous or crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester in an inert solvent for 1-120 hours, and thereafter isolating the crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester.

As solvent a polar protic solvent, or a dipolar aprotic solvent or an ether type solvent can be used.

As polar protic solvent a lower alkanol (preferably methanol, ethanol, 2-propanol), water or a mixture of said solvents can be used. It is particularly preferred to use ethanol, 2-propanol, water or a mixture of 2-propanol and water as polar protic solvent.

As dipolar aprotic solvent acetone, acetonitrile, ethyl acetate, dimethyl formamide, dimethyl sulfoxide or hexamethyl phosphoric acid triamide can be used. One may use preferably acetonitrile.

As ether type solvent preferably acetonitrile can be used.

The exact reaction conditions used in the preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester can be experimentally ascertained.

In the course of the above processes a) and b) amorphous or crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester is dissolved in an inert solvent under reflux, the solution is kept at said temperature for some minutes, then cooled to room temperature and allowed to stand. The crystals are isolated by filtration or centrifuging.

According to process c) amorphous or crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester is suspended in an inert solvent for 1-120 hours, whereupon the precipitated crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester is isolated by filtration or centrifuging. The duration of the suspending step depends on the solvent used and can be experimentally established.

According to a further aspect of the invention there is provided crystalline form II (4R-cis)-6-[2-[3-phenyl-4-(phenyl-carbamoyl)-2-(4-fluoro-phenyl)-5-(1-methyl-ethyl)- pyrrol-1-yl]-ethyl]-2,2-dimethyl-[1,3]dioxane-4-yl-acetic acid-tertiary butyl ester characterized by the X-ray powder diffraction pattern expressed in Table 2 and FIG. 2, measured using CuK$_\alpha$ radiation:

TABLE 2

Position of diffraction lines and relative intensities (>10% of polymorph II)

| Peak No. | 2*th [deg] | d(hkl) [Å] | I(abs) [cts] | I(rel) [%] |
|---|---|---|---|---|
| 1 | 6.45 | 13.7061 | 463 | 18.54 |
| 2 | 6.94 | 12.7356 | 1639 | 65.64 |
| 3 | 11.43 | 7.7393 | 1331 | 53.30 |
| 4 | 12.21 | 7.2491 | 1039 | 41.61 |
| 5 | 12.53 | 7.0652 | 866 | 34.68 |
| 6 | 13.17 | 6.7223 | 1247 | 49.94 |
| 7 | 14.29 | 6.1983 | 2497 | 100.00 |
| 8 | 15.05 | 5.8866 | 998 | 39.97 |
| 9 | 16.45 | 5.3873 | 625 | 25.03 |
| 10 | 17.50 | 5.0665 | 1837 | 73.57 |
| 11 | 17.85 | 4.9690 | 2325 | 93.11 |
| 12 | 18.65 | 4.7584 | 1685 | 67.48 |
| 13 | 19.03 | 4.6626 | 1105 | 44.25 |
| 14 | 19.97 | 4.4468 | 1367 | 54.75 |
| 15 | 20.16 | 4.4055 | 1457 | 58.35 |
| 16 | 20.90 | 4.2495 | 946 | 37.89 |
| 17 | 21.36 | 4.1606 | 1616 | 64.72 |
| 18 | 21.99 | 4.0426 | 1169 | 46.82 |
| 19 | 22.24 | 3.9972 | 1486 | 59.51 |
| 20 | 22.74 | 3.9111 | 1471 | 58.91 |
| 21 | 23.80 | 3.7391 | 279 | 11.17 |
| 22 | 24.37 | 3.6526 | 422 | 16.90 |
| 23 | 24.69 | 3.6060 | 323 | 12.94 |
| 24 | 25.35 | 3.5141 | 628 | 25.15 |
| 25 | 25.71 | 3.4648 | 635 | 25.43 |
| 26 | 26.41 | 3.3750 | 332 | 13.30 |
| 27 | 27.73 | 3.2172 | 483 | 19.34 |
| 28 | 28.05 | 3.1812 | 395 | 15.82 |
| 29 | 28.64 | 3.1173 | 449 | 17.98 |
| 30 | 29.33 | 3.0452 | 409 | 16.38 |
| 31 | 29.77 | 3.0010 | 400 | 16.02 |
| 32 | 30.48 | 2.9330 | 249 | 9.97 |

The powder diffraction pattern of the new crystalline form II is determined under the conditions described in connection with crystalline form I.

According to a still further aspect of the invention there is provided a process for the preparation of crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester which comprises a) dissolving amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester in an inert solvent under heating, and thereafter crystallizing and isolating crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester; or b) dissolving crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester in an inert solvent under heating, and thereafter crystallizing and isolating crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester; or c) reacting (4R-cis)-1,1-dimethyl-ethyl-6-(2-amino-ethyl)-2,2-dimethyl-1,3-dioxane-4-acetate of the Formula II with 2-[1-phenyl-2-(4-fluoro-phenyl)-2-oxo-ethyl]-4-methyl-N-methyl-3-oxo-pentanamide of the Formula III in a 1:4:1 mixture of toluene, heptane and tetrahydrofurane in the presence of pivalic acid as catalyst, adding to the reaction mixture at the end of the reaction diisopropyl ether, and thereafter isolating crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester.

Processes a) and b) can be carried out under the conditions described in connection with the preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester. As inert solvent preferably apolar solvents, particularly cyclohexane, heptane, hexane, toluene or a mixture of said solvents can be used. In addition to the maintenance of the apolar character, the inert solvent can contain a small amount of an ether type solvent (e.g. diisopropyl ether or tetrahydrofurane).

The exact reaction conditions used in course of the preparation of crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester are determined experimentally.

According to process c) to the reaction mixture obtained as a result of the reaction of the compounds of the Formulae II and III carried out in a 1:4:1 mixture of toluene, heptane and tetrahydrofurane in the presence of pivalic acid as catalyst diisopropyl ether is added after the reaction having been completed, whereupon crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester is isolated.

It appears from the aforesaid the polymorphs I and II can be mutually converted into each other.

The present invention enables the preparation of (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester having uniform crystal structure in a highly pure form.

The present invention shows the following advantages:
a readily filtrable and dryable product having technologically uniform filtration and drying properties is obtained;
the recrystallization process and the morphologically uniform crystal structure enables the preparation of a highly pure product;
the purity determined by HPLC is >99.5%;
the morphologically uniform product of the invention is stable after storage for a long period of time;
no special storing conditions are needed;
the invention process can be readily scaled up and is suitable for industrial scale production.

Further details of the present invention are to be found in the following Examples without limiting the scope of invention to said Examples.

EXAMPLE 1

Preparation of crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester from (4R-cis)-6-[2-[3-phenyl-4-(phenyl-carbamoyl)-2-(4-fluoro-phenyl)-5-(1-methylethyl)-pyrrol-1-yl]-ethyl]-2,2-dimethyl-[1,3]dioxane-4-yl-acetic acid-tertiary butyl ester containing crystalline form I Into a 10 ml round-bottomed flask equipped with a reflux condenser and a thermometer 2 g of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and 5 ml of cyclohexane are weighed in. The mixture is refluxed for 5 minutes, cooled to room temperature and allowed to stand overnight. The suspension is filtered, the product is washed and dried at 35-40° C. until constant weight. Thus 1.87 g of the title product are obtained. M.p.: 128-130° C.

EXAMPLE 2

Preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester from (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester containing crystalline form II Into a 25 ml round-flask equipped with a reflux condenser and a thermometer 2 g of crystalline form II (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3] dioxane-4-yl-acetic acid-tertiary butyl ester and 5 ml of ethanol are weighed in. The mixture is refluxed for 5 minutes, cooled to room temperature and allowed to stand overnight. The suspension is filtered, the product is washed and dried at 35-40° C. until constant weight. Thus 1.81 g of the title product are obtained. M.p.: 140-142° C.

EXAMPLE 3

Preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester Into a 10 ml round-bottomed flask equipped with a reflux condenser and a thermometer 2 g of amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and 3 ml of acetonitrile are weighed in. The mixture is refluxed for 5 minutes, cooled to room temperature and allowed to stand overnight. The suspension is filtered, the product is washed and dried at 35-40° C. until constant weight. Thus 1.84 g of the title product are obtained. M.p.: 140-142° C.

EXAMPLE 4

Preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester Into a 10 ml round-bottomed flask equipped with a reflux condenser and a thermometer 2 g of amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and 3.5 ml of 2-propanol are weighed in. The mixture is refluxed for 5 minutes, cooled to room temperature and allowed to stand overnight. The suspension is filtered, the product is washed and dried at 35-40° C. until constant weight. Thus 1.85 g of the title product are obtained. M.p.: 140-142° C.

EXAMPLE 5

Preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester Into a 100 ml round-bottomed flask equipped with a reflux condenser and a thermometer 2 g of amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and 47 ml of diisopropyl ether are weighed in. The mixture is refluxed for 5 minutes, cooled to room temperature and allowed to stand overnight. The suspension is filtered, the product is washed and dried at 3 5-40° C. until constant weight. Thus 1.74 g of the title product are obtained. M.p.: 140-142° C.

EXAMPLE 6

Preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester Into a 250 ml round-bottomed flask equipped with a reflux condenser and a thermometer 2 g of amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and 130 ml of a 2:1 mixture of 2-propanol and water are weighed in. The mixture is refluxed for 5 minutes, cooled to room temperature and allowed to stand overnight. The suspension is filtered, the product is washed and dried at 35-40° C. until constant weight. Thus 1.80 g of the title product are obtained. M.p.: 140-142° C.

EXAMPLE 7

Preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester Into a 50 ml round-bottomed flask equipped with a reflux condenser and a thermometer 2 g of amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester and 19 ml of a 4:1 mixture of 2-propanol and water and weighed in. The mixture is refluxed for 5 minutes, cooled to room temperature and allowed to stand overnight. The suspension is filtered, the product is washed and dried at 35-40° C. until constant weight. Thus 1.86 g of the title product are obtained. M.p.: 140-142° C.

We claim:

1. Crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester of the Formula

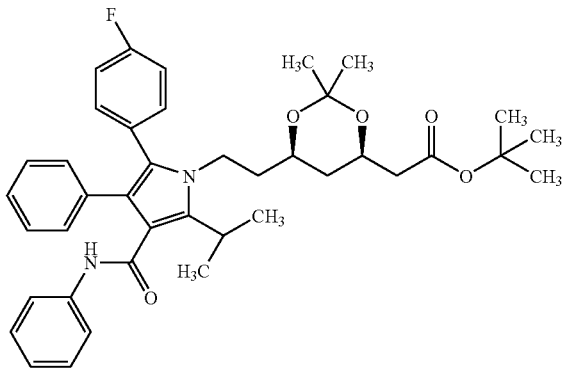

(I)

having a melting point range of 140–142° C., characterized by the X-ray powder diffraction pattern expressed in Table 1 and FIG. 1, measured using CuK$_\alpha$ radiation:

TABLE 1

Position of diffraction lines and relative intensities (>10% of polymorph I)

| Peak No. | 2*th [deg] | d(hkl) [Å] | I(abs) [cts] | I(rel) [%] |
|---|---|---|---|---|
| 1 | 9.85 | 8.9800 | 6701 | 100.00 |
| 2 | 11.20 | 7.8983 | 996 | 14.86 |
| 3 | 13.14 | 6.7401 | 771 | 11.51 |
| 4 | 15.89 | 5.5793 | 1043 | 15.56 |
| 5 | 17.76 | 4.9940 | 2565 | 38.28 |
| 6 | 18.29 | 4.8508 | 2710 | 40.44 |
| 7 | 18.69 | 4.7483 | 2152 | 32.11 |
| 8 | 19.17 | 4.6300 | 3325 | 49.62 |
| 9 | 19.66 | 4.5155 | 983 | 14.67 |
| 10 | 20.24 | 4.3865 | 10064 | 15.88 |
| 11 | 21.10 | 4.2107 | 671 | 10.01 |
| 12 | 21.49 | 4.1351 | 1362 | 20.33 |
| 13 | 22.05 | 4.0310 | 889 | 13.27 |
| 14 | 22.90 | 3.8836 | 863 | 12.88 |

TABLE 1-continued

Position of diffraction lines and relative intensities (>10% of polymorph I)

| Peak No. | 2*th [deg] | d(hkl) [Å] | I(abs) [cts] | I(rel) [%] |
|---|---|---|---|---|
| 15 | 26.41 | 3.3749 | 681 | 10.16 |
| 16 | 26.95 | 3.3080 | 597 | 8.91 |
| 17 | 27.89 | 3.1995 | 612 | 9.13. |

2. Process for the preparation of crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester according to claim 1 which comprises a) dissolving amorphous (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester in an inert solvent under heating, and thereafter crystallizing and isolating the crystalline form I (4R-cis)-6-[2-[3-phenyl-4-(phenyl-carbamoyl)-2-(4-fluoro-phenyl)-5-(1-methyl-ethyl)-pyrrol-1-yl]-ethyl]-2,2-dimethyl-[1,3]dioxane-4-yl-acetic acid-tertiary butyl ester.

3. Process according to claim 2 which comprises using as solvent a polar protic solvent, or a dipolar aprotic solvent or an ether type solvent.

4. Process according to claim 3 which comprises using as protic solvent a lower alkanol or water or a mixture of said solvents.

5. Process according to claim 4 which comprises using methanol, ethanol, 2-propanol, water or a mixture of 2-propanol and water.

6. Process according to claim 3 which comprises using as dipolar aprotic solvent acetone, acetonitrile, ethyl acetate, dimethyl formamide, dimethyl sulfoxide or hexamethyl phosphoric acid triamide.

7. Process according to claim 3 which comprises using diisopropyl ether as ether type solvent.

* * * * *